(12) United States Patent
Ci

(10) Patent No.: US 10,485,838 B2
(45) Date of Patent: Nov. 26, 2019

(54) CHINESE HERBAL ORAL PASTE FOR CONDITIONING YIN DEFICIENCY CONSTITUTION AND PROCESSING METHOD THEREFOR

(71) Applicant: Zhonghua Ci, Beijing (CN)

(72) Inventor: Zhonghua Ci, Beijing (CN)

(*) Notice: Subject to any disclaimer, the term of this patent is extended or adjusted under 35 U.S.C. 154(b) by 0 days.

(21) Appl. No.: 15/967,003

(22) Filed: Apr. 30, 2018

(65) Prior Publication Data

US 2019/0192606 A1  Jun. 27, 2019

(30) Foreign Application Priority Data

Dec. 26, 2017  (CN) .......................... 2017 1 1429037

(51) Int. Cl.

| | | |
|---|---|---|
| A61K 36/00 | (2006.01) | |
| A61K 36/804 | (2006.01) | |
| A61K 36/815 | (2006.01) | |
| A61K 36/8984 | (2006.01) | |
| A61K 36/8969 | (2006.01) | |
| A61K 36/8968 | (2006.01) | |
| A61K 36/8967 | (2006.01) | |
| A61K 36/8965 | (2006.01) | |
| A61K 36/65 | (2006.01) | |
| A61K 36/638 | (2006.01) | |
| A61K 36/484 | (2006.01) | |
| A61K 36/40 | (2006.01) | |
| A61K 36/232 | (2006.01) | |
| A61K 36/076 | (2006.01) | |
| A61K 47/26 | (2006.01) | |
| A61K 47/42 | (2017.01) | |
| A61K 9/00 | (2006.01) | |
| A61P 1/14 | (2006.01) | |
| A61K 36/8945 | (2006.01) | |
| A61K 45/06 | (2006.01) | |
| A61K 9/06 | (2006.01) | |
| A61K 35/50 | (2015.01) | |

(52) U.S. Cl.
CPC .......... *A61K 36/804* (2013.01); *A61K 9/0053* (2013.01); *A61K 9/0056* (2013.01); *A61K 9/06* (2013.01); *A61K 35/50* (2013.01); *A61K 36/076* (2013.01); *A61K 36/232* (2013.01); *A61K 36/40* (2013.01); *A61K 36/484* (2013.01); *A61K 36/638* (2013.01); *A61K 36/65* (2013.01); *A61K 36/815* (2013.01); *A61K 36/8945* (2013.01); *A61K 36/8965* (2013.01); *A61K 36/8967* (2013.01); *A61K 36/8968* (2013.01); *A61K 36/8969* (2013.01); *A61K 36/8984* (2013.01); *A61K 45/06* (2013.01); *A61K 47/26* (2013.01); *A61K 47/42* (2013.01); *A61P 1/14* (2018.01); *A61K 2236/331* (2013.01)

(58) Field of Classification Search
None
See application file for complete search history.

*Primary Examiner* — Qiuwen Mi

(74) *Attorney, Agent, or Firm* — Novick, Kim & Lee, PLLC; Allen Xue

(57) ABSTRACT

The present application discloses a Chinese herbal oral paste for conditioning yin deficiency constitution. The Chinese herbal oral paste includes the following components: coastal glehnia root, prepared rehmannia root, dogberry, Chinese yam, cortex moutan, fuling, radix asparagi, fruit of Chinese magnoliavine, lycium barbarum, rhizoma alismatis, tremella, finger citron, fructus tribuli, ophiopogonis radix, glossy privet fruit, amomum villosum, dendrobium nobile, lilium brownii, angelica, radix paeoniae alba, licorice, radix scrophulariae, thunberg fritillary bulb, polygonatum odoratum, semen sesami nigrums, mulberry, turtle shell gelatin, tortoise-plastron gelatin, donkey-hide gelatin, xylitol, and American ginseng. The Chinese herbal oral paste of the present disclosure has a higher drug concentration and good taste, is particularly suitable for health preserving in winter and conditioning the yin deficiency constitution, will not create negative effects or harm to the human body at all, and is capable of achieving certain efficacy of strengthening physical health.

20 Claims, 1 Drawing Sheet

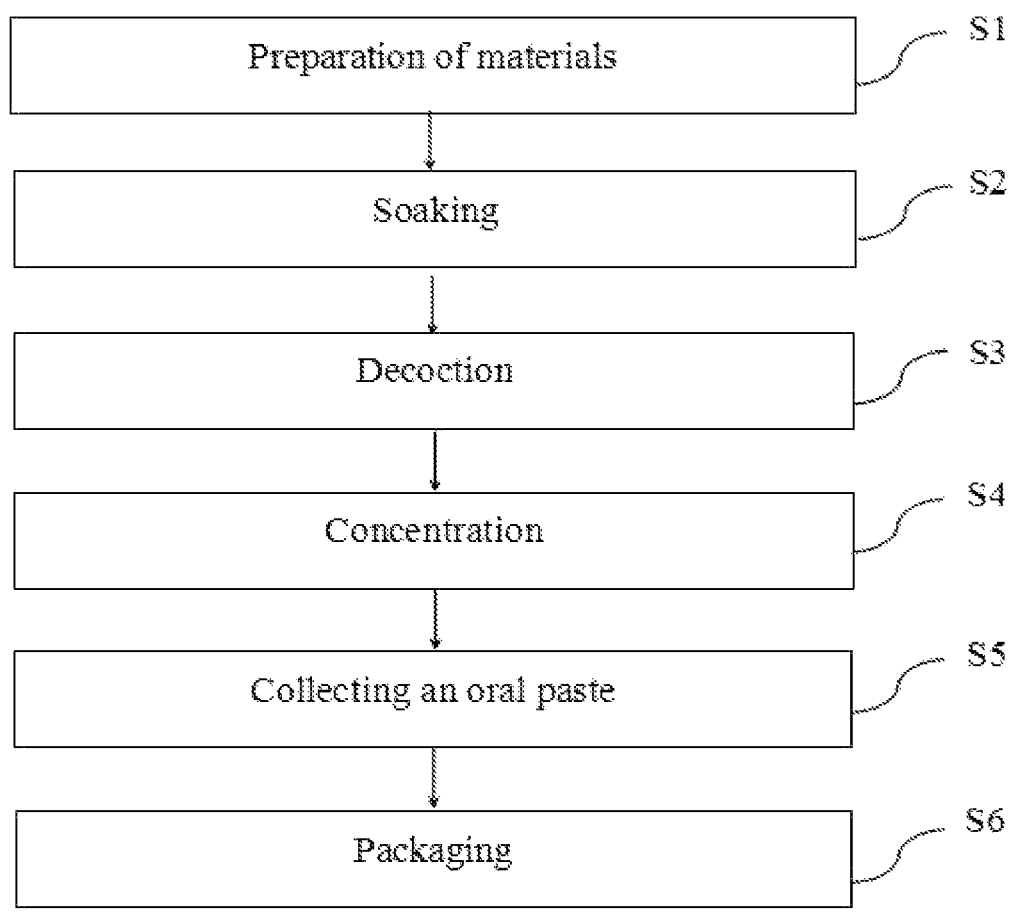

CHINESE HERBAL ORAL PASTE FOR CONDITIONING YIN DEFICIENCY CONSTITUTION AND PROCESSING METHOD THEREFOR

TECHNICAL FIELD

The present disclosure relates to the field of health foods, and particularly to a Chinese herbal oral paste for conditioning yin deficiency constitution and a processing method therefor.

BACKGROUND

In *Classification and Determination of Constitution in Traditional Chinese Medicine*, the China Association of Chinese Medicine classifies constitutions of the human body into nine types, including yin-yang harmony constitution, yang deficiency constitution, yin deficiency constitution, qi deficiency constitution, phlegm-dampness constitution, damp-heat constitution, qi depression constitution, blood stasis constitution, and allergic constitution, most of which belong to sub-healthy states.

The yin deficiency constitution means that, when internal organs are dysfunctional, the syndromes of yin-fluid deficiency in the body and production of endogenous heat due to yin deficiency will easily occur, which are usually represented by emaciation of the body, tidal reddening of two cheeks, feverishness in palms and soles, tidal fever and night sweating, upset irritability, xerostomia, hair and skin dryness, and dry and red tongue with little or even no coating, which are mainly caused by invasion of pathogenic dryness-heat, overeating of febrile and dry food, excessive grief and sorrow, intemperance in sexual life and long illness. The tendency of morbidity is: being susceptible to consumptive disease, seminal emission, insomnia, etc., being resistant to winter but nonresistant to summer, and being nonresistant to summer, heat, and pathogenic dryness.

Such sub-healthy constitution as yin deficiency constitution belongs to chronic diseases and has a relatively long disease course, and requires a long-term medication and gradual conditioning, in order to achieve the effects of tonifying qi (vital energy) and nourishing qi. The drug forms commonly used in the traditional Chinese medicine are decoctions and Chinese patent medicine such as pills and the like. Decoctions usually have relatively good efficacy, but the administration thereof is complicated, and the taste thereof is poor. If the decoctions need to be prepared for a long time, it is difficult for a patient to keep taking the decoctions. Moreover, the efficacy of the pills is relatively poor.

It is mentioned in the Inner Canon of the Yellow Emperor that "the superior physician prevents illness, the mediocre physician attends to impending illness, and the inferior physician treats actual illness", wherein the phrase "prevent illness" means taking corresponding measures to prevent the occurrence and development of diseases. The body constitution determines the health of people and susceptibility to diseases. It is believed in the traditional Chinese medicine that since the human beings live in the natural world, physiological functions of the human body usually change with seasons, that is, "correspondence between man and nature". Winter is the season when the human body "stores energies", thus appropriate nourishment can enhance the constitution, ward off diseases and strengthen the body, and prolong life, that is, conditioning in winter or nourishing in winter commonly mentioned in the traditional Chinese medicine. For the sub-healthy population with yin deficiency constitution, a solid oral paste with a higher drug concentration and good taste, and being convenient to carry more meets requirements of modern people.

SUMMARY

A main object of the present disclosure is to provide a Chinese herbal nourishing product suitable for conditioning in winter so as to treat yin deficiency constitution.

In order to achieve the above object, according to one aspect of the present disclosure, there is provided a Chinese herbal oral paste for conditioning yin deficiency constitution.

The Chinese herbal oral paste for conditioning yin deficiency constitution according to the present disclosure includes the following components in parts by weight: 10-30 parts of coastal glehnia root, 2-25 parts of prepared rehmannia root, 5-25 parts of dogberry, 5-25 parts of Chinese yam, 6-16 parts of cortex moutan, 5-15 parts of fuling, 5-15 parts of radix asparagi, 1-5 parts of fruit of Chinese magnoliavine, 5-15 parts of lycium barbarum, 4-12 parts of rhizoma alismatis, 10-30 parts of tremella, 3-9 parts of finger citron, 6-24 parts of fructus tribuli, 5-15 parts of ophiopogonis radix, 8-22 parts of glossy privet fruit, 1-5 parts of amomum villosum, 10-30 parts of dendrobium nobile, 11-29 parts of lilium brownii, 5-15 parts of angelica, 7-23 parts of radix paeoniae alba, 1-5 parts of licorice, 5-15 parts of radix scrophulariae, 2-10 parts of thunberg fritillary bulb, 5-15 parts of polygonatum odoratum, 7-23 parts of semen sesami nigrums, 5-15 parts of mulberry, 10-30 parts of turtle shell gelatin, 10-30 parts of tortoise-plastron gelatin, 4-17 parts of donkey-hide gelatin, 20-40 parts of xylitol, and 5-15 parts of American ginseng.

Furthermore, the Chinese herbal oral paste for conditioning yin deficiency constitution according to the present disclosure includes: 15-25 parts by weight of coastal glehnia root, 10-20 parts by weight of prepared rehmannia root, 10-20 parts by weight of dogberry, 10-20 parts by weight of Chinese yam, 7-13 parts by weight of cortex moutan, 7-13 parts by weight of fuling, 7-13 parts by weight of radix asparagi, 2-4 parts by weight of fruit of Chinese magnoliavine, 7-13 parts by weight of lycium barbarum, 6-10 parts by weight of rhizoma alismatis, 15-25 parts by weight of tremella, 4-8 parts by weight of finger citron, 10-20 parts by weight of fructus tribuli, 7-13 parts by weight of ophiopogonis radix, 11-19 parts by weight of glossy privet fruit, 2-4 parts by weight of amomum villosum, 15-25 parts by weight of dendrobium nobile, 15-25 parts by weight of lilium brownii, 7-13 parts by weight of angelica, 10-20 parts by weight of radix paeoniae alba, 2-4 parts by weight of licorice, 7-13 parts by weight of radix scrophulariae, 4-8 parts by weight of thunberg fritillary bulb, 7-13 parts by weight of polygonatum odoratum, 10-20 parts by weight of semen sesami nigrums, 7-13 parts by weight of mulberry, 15-25 parts by weight of turtle shell gelatin, 15-25 parts by weight of tortoise-plastron gelatin, 7-13 parts by weight of donkey-hide gelatin, 25-35 parts by weight of xylitol, and 7-13 parts by weight of American ginseng.

Furthermore, the Chinese herbal oral paste for conditioning yin deficiency constitution according to the present disclosure includes: 20 parts by weight of coastal glehnia root, 15 parts by weight of prepared rehmannia root, 15 parts by weight of dogberry, 15 parts by weight of Chinese yam, 10 parts by weight of cortex moutan, 10 parts by weight of fuling, 10 parts by weight of radix asparagi, 3 parts by weight of fruit of Chinese magnoliavine, 10 parts by weight of lycium barbarum, 8 parts by weight of rhizoma alismatis, 20 parts by weight of tremella, 6 parts by weight of finger citron, 15 parts by weight of fructus tribuli, 10 parts by weight of ophiopogonis radix, 15 parts by weight of glossy privet fruit, 3 parts by weight of amomum villosum, 20 parts by weight of dendrobium nobile, 20 parts by weight of lilium brownii, 10 parts by weight of angelica, 15 parts by weight of radix paeoniae alba, 3 parts by weight of licorice, 10 parts by weight of radix scrophulariae, 6 parts by weight of thunberg fritillary bulb, 10 parts by weight of polygonatum odoratum, 15 parts by weight of semen sesami nigrums, 10 parts by weight of mulberry, 20 parts by weight of turtle shell gelatin, 20 parts by weight of tortoise-plastron gelatin, 10 parts by weight of donkey-hide gelatin, 30 parts by weight of xylitol, and 10 parts by weight of American ginseng.

In order to achieve the above object, according to the other aspect of the present disclosure, there is a processing method for a Chinese herbal oral paste for conditioning yin deficiency constitution provided.

The processing method for a Chinese herbal oral paste for conditioning yin deficiency constitution according to the present disclosure includes the following steps in sequence: preparation of materials, soaking, decoction, concentration, and collecting an oral paste.

Furthermore, the step of preparation of materials is: measuring raw materials of formula ratio according to composition of the Chinese herbal oral paste, and washing raw materials, except turtle shell gelatin, tortoise-plastron gelatin, donkey-hide gelatin, and xylitol, for subsequent use.

Furthermore, the soaking step is: soaking the cleaned raw materials with 8-10 folds of water for 8-15 h, with the water over the raw materials by 10-20 cm.

Furthermore, the decoction step is: decocting the soaked drug materials over flame, firstly boiling the drug materials with high heat to sufficiently expand, then boiling the drug materials with low heat for 1-2 hours of decoction, then filtering drug juice with gauze, then soaking filtered dregs of decoction with clear water and decocting the soaked dregs of decoction with low heat for 1 hour, thus repeating 2-4 times, then combining the filtered drug juice, and squeezing and filtering the dregs to obtain squeezed juice; combining decoction juice with the squeezed juice, followed by static settlement for 2 h, and filtering, to obtain a supernatant liquid for subsequent use.

Furthermore, the concentration step is: boiling and skimming the supernatant liquid resulted in the decoction step, followed by stirring while decocting and concentrating with low heat, until the drug liquid does not disperse when being dropped on paper, to obtain a vegetarian paste.

Furthermore, the step of collecting an oral paste is: pouring xylitol, melted turtle shell gelatin, tortoise-plastron gelatin, and donkey-hide gelatin into the vegetarian paste respectively, stirring them continuously with a shovel while cooking them slowly with low heat, until the juice can coagulate into beads and not disperse when dropped into clear water, then canning the resulted oral paste.

The melting step is: smashing lumps of turtle shell gelatin, tortoise-plastron gelatin, and donkey-hide gelatin into small gelatin pieces or gelatin powder, soaking and softening the small gelatin pieces or the gelatin powder in Shaoxing wine, water bath heating the softened small gelatin pieces or gelatin powder in a steamer until they are completely melted.

The Chinese herbal oral paste of the present disclosure has a higher drug concentration and good taste, is particularly suitable for health preserving in winter and conditioning the yin deficiency constitution, will not create negative effects or harm to the human body at all, and is capable of achieving certain efficacy of strengthening physical health.

BRIEF DESCRIPTION OF THE DRAWINGS

The accompanying drawing, which constitutes a part of the present application, is used to provide a further understanding of the present disclosure, so that other features, objects, and advantages of the present application become more obvious. The illustrative drawings for embodiments of the present disclosure and the description thereof are used to explain the present disclosure, rather than constitute an improper limitation on the present disclosure. In the drawing, FIG. 1 is a flow chart of a processing technology for a Chinese herbal oral paste of an embodiment of the present disclosure.

DETAILED DESCRIPTION OF THE EMBODIMENTS

In order to enable a person skilled in the art to better understand the solutions of the present application, the technical solutions of the embodiments of the present disclosure will be described clearly and completely below with reference to the accompanying drawing of the embodiments of the present application. Apparently, the embodiments described are merely for some of the embodiments of the present application, rather than all of the embodiments. All the other embodiments that are obtained by a person skilled in the art without inventive effort on the basis of the embodiments of the present application shall be covered by the protection scope of the present application.

In addition, the term "comprise" and any variant thereof are intended to cover non-exclusive inclusion, for example, a product comprising a series of raw materials or a method comprising a series of steps is not necessarily limited to the raw materials or the steps listed clearly, but can include other steps or raw materials that are not clearly listed or are inherent to the method and product.

It should be noted that the embodiments of the present application and the features of the embodiments can be combined with each other if there is no conflict. The present application will be described in detail below in combination with the embodiments.

The present disclosure provides a Chinese herbal oral paste for conditioning yin deficiency constitution, including the following components: coastal glehnia root, prepared rehmannia root, dogberry, Chinese yam, cortex moutan, fuling, radix asparagi, fruit of Chinese magnoliavine, lycium barbarum, rhizoma alismatis, tremella, finger citron, fructus tribuli, ophiopogonis radix, glossy privet fruit, amomum villosum, dendrobium nobile, lilium brownii, angelica, radix paeoniae alba, licorice, radix scrophulariae, thunberg fritillary bulb, polygonatum odoratum, semen sesami nigrums, mulberry, turtle shell gelatin, tortoise-plastron gelatin, donkey-hide gelatin, xylitol, and American ginseng.

Coastal glehnia root is sweet and slightly bitter in flavor and slightly cold in nature, acts on lung and spleen, nourishes yin and clears lung, eliminates phlegm and relieves cough, and is used for lung-heat dry cough, chronic consumptive cough, yin-damage dry throat, and thirst.

Prepared rehmannia root is sweet in flavor and warm in nature, acts on liver and kidney, nourishes blood and moistens dryness, replenishes essence and supplements marrow, and is used for blood-deficiency etiolation, vertigo and palpitation, irregular menstruation, flooding, liver-kidney yin depletion, tidal fever and night sweating, gonobolia and impotence, infertility, irregular menstruation, metrorrhagia embolism in blood, soreness and weakness of waist and knees, tinnitus and hearing loss, dizziness, premature graying of hair, consumptive thirst, constipation, and kidney-deficiency panting.

Dogberry is sour and astringent in flavor and slightly warm in nature, acts on liver and kidney, nourishes liver and kidney, promotes astriction and relieves desertion, and is used for vertigo and tinnitus, soreness and weakness of waist and knees, impotence and gonobolia, enuresis and frequent urination, metrorrhagia and leucorrhoea, hyperhidrosis prostration, and internal-heat consumptive thirst.

Chinese yam is sweet in flavor, neutral in nature, and non-toxic, acts on spleen, lung, and kidney, strengthens spleen and stomach, nourishes lung qi, tonifies kidney essence, nourishes physical health, renders good hearing and eyesight and delays senility upon long administration, and is used for reduced spleen-deficiency appetite, loose stool diarrhea, lung-deficiency asthma, gonobolia and frequent urination, and yin-deficiency consumptive thirst.

Cortex moutan is bitter and acrid in flavor and slightly cold in nature, acts on heart, liver, and stomach, removes heat to cool blood, removes blood stasis, eliminates deficient heat, and is used for blood-heat haematemesis, eruption, yin-deficiency internal heat, anhidrotic steaming bone, amenorrhea and algomenorrhea, traumatic injury, swelling pain of skin and external diseases, and intestinal carbuncle and stomachache.

Fuling is sweet and light in flavor and neutral in nature, acts on heart, lung, spleen, and kidney, clears dampness and promotes diuresis, tonifies spleen, calms mind, and is used for edema and scanty urine, phlegm and fluid retention, vertigo and palpitation, reduced spleen-deficiency appetite, loose stool and diarrhea, uneasiness, and palpitation and insomnia.

Radix asparagi is sweet and bitter in flavor and cold in nature, acts on lung and kidney, nourishes yin and moistens dryness, clears lung and promotes the secretion of body fluid, and is used for lung-dryness dry cough, pertussis and sticky phlegm, soreness and ache of waist and knees, steaming bone hectic fever, internal heat consumptive thirst, febrile disease and body fluid impairment, throat dryness and thirst, and constipation due to intestinal dryness.

Fruit of chinese magnoliavine is sour in flavor and warm in nature, acts on lung, kidney, and heart, astringes lung, nourishes kidney, promotes the secretion of body fluid, constrains sweating, arrests seminal emission, and is used for kidney-deficiency asthma, mouth dryness and thirst, spontaneous perspiration, night sweating, internal lesion caused by overexertion and emaciation, wet dream and spermatorrhea, and chronic diarrhea and dysentery.

Lycium barbarum is sweet in flavor and neutral in nature, acts on liver and kidney, has the efficacies of nourishing kidney and essence, and nourishing liver to improve eyesight, and is used for liver and kidney yin deficiency, soreness and weakness of waist and knees, dizziness, visual deterioration, consumptive thirst, and spermatorrhea.

Rhizoma alismatis is sweet in flavor and cold in nature, acts on kidney and bladder, alleviates water retention, promotes diuresis, reduces heat, and is used for difficult urination, edema distention, vomiting, diarrhea, phlegm-fluid retention, dermatophytosis, gonorrhea, and hematuria.

Tremella is sweet and light in flavor, neutral in nature, and non-toxic, acts on lung, stomach, and kidney, supplements lung and tonifies qi, nourishes yin and moistens dryness, and is used for weakness after illness, chronic lung-deficiency cough, blood-stained sputum, metrorrhagia and metrostaxis, constipation, hypertension, and vascular sclerosis.

Finger citron is acrid, bitter, and sour in flavor and warm in nature, acts on liver, spleen, stomach, and lung, soothes liver and regulates qi, harmonizes the stomach to relieve pain, eliminates dampness and phlegm, and is used for qi-stagnation in the liver and stomach, distending pain in chest and hypochondrium, stomach distention and fullness, reduced appetite and vomiting, and cough with excessive phlegm.

Fructus tribuli is bitter and acrid in flavor and neutral in nature, acts on liver, calms liver and resolves depression, dispels wind and improves eyesight, and is used for hypertension vertigo and headache, liver depression and hypochondriac pain, headache due to pathogenic wind-heat, sore red swollen eyes, skin itch and other diseases.

Ophiopogonis radix is sweet and slightly bitter in flavor and slightly cold in nature, acts on lung, stomach, and heart, nourishes yin and moistens lung, tonifies stomach and promotes the secretion of body fluid, clears away heat fire and relieves restlessness, and is used for lung-dryness dry cough, pulmonary abscess, yin-deficiency overstrained cough, body fluid impairment thirst, consumptive thirst, dysphoria insomnia, sore throat, constipation due to intestinal dryness, and blood-heat haematemesis.

Glossy privet fruit is sweet and bitter in flavor and cold in nature, acts on liver and kidney, nourishes liver and kidney, improves eyesight, clears away asthenic fever, and is used for dizziness, premature graying of hair, blurred vision, and fever due to yin deficiency.

Amomum villosum is acrid in flavor and warm in nature, acts on spleen, stomach, and kidney, promotes circulation of qi, harmonizes stomach, refreshes spleen, and is used for stomachache and abdominal distension, anorexia and dyspepsia, dysphagia and vomiting, cold diarrhea, and fetal movement.

Dendrobium nobile is sweet flavor and slightly cold in nature, acts on stomach and kidney, benefits stomach and promotes the secretion of body fluid, nourishes yin and clears away heat, and is used for febrile disease and body fluid impairment, mouth dryness and polydipsia, lack of stomach yin, reduced appetite and vomiturition, persistent deficiency-heat after illness, yin-deficiency fire excess, steaming bone consumptive fever, blurred vision, and motor impairment of muscles and bones.

Lilium brownii is sweet in flavor and cold in nature, acts on heart and lung, nourishes yin and moistens lung, clears away heart fire and calms mind, and is used for yin-deficiency dry cough, overstrained cough and hemoptysis, dysphoria and pavor, insomnia and dreamful sleep, and trance.

Angelica is sweet and acrid in flavor and warm in nature, acts on liver, heart, and spleen, replenishes blood and invigorates the circulation of blood, regulates menstruation and relieves pain, relaxes bowel, and is used for blood-deficiency etiolation, vertigo and palpitation, irregular menstruation, amenorrhea and dysmenorrhea, deficiency-cold stomachache, rheumatic arthralgia, traumatic injury, ulcer and skin and external diseases, and constipation due to intestinal dryness.

Radix paeoniae alba is bitter and sour in flavor and slightly cold in nature, acts on liver and spleen, soothes liver and relieves pain, replenishes blood and regulates menstruation, astringes yin and resists sweating, and is used for headache and vertigo, hypochondriac pain, stomachache, four-limb stiffness, blood-deficiency etiolation, irregular menstruation, spontaneous perspiration, and night sweating.

Licorice is sweet in flavor and neutral in nature, acts on heart, lung, spleen, and stomach, supplements spleen and tonifies qi, removes heat and toxic matters, eliminates phlegm and relieves cough, relieves spasm and alleviates pain, moderates various drugs, and is used for weakness of spleen and stomach, lassitude and asthenia, palpitation and short of breath, cough with excessive phlegm, abdominal distention, four-limb spasm and pain, carbuncle, and alleviation of drug toxicity and intensity.

Radix scrophulariae is sweet, bitter, and salty in flavor and slightly cold in nature, acts on spleen, stomach, and kidney, removes heat to cool blood, nourishes yin to lessen fire, clears away toxic matters and removes stasis, and is used for warm heat and febrile diseases, Nutrient, Blood, general fever, polydipsia, deep red tongue, eruption, steaming bone consumptive thirst, dysphoria insomnia, body fluid impairment and constipation, eye dryness and dizziness, sore throat, crewels and subcutaneous nodule, and carbuncle.

Thunberg fritillary bulb is bitter in flavor and cold in nature, acts on lung and heart, removes heat to eliminate phlegm and relieve cough, clears away toxic matters to remove stasis and resolves carbuncle, and is used for cough due to wind-heat, pyrophlegm cough, pulmonary abscess, acute mastitis, crewels, and carbuncle.

Polygonatum odoratum is sweet in flavor and neutral in nature, acts on lung and stomach, nourishes yin, moistens dryness, promotes the secretion of body fluid and quenches thirst, and is used for lung and stomach yin injury, dryness-heat cough, throat dryness and thirst, and internal-heat consumptive thirst.

Semen sesami nigrums is sweet in flavor and neutral in nature, acts on liver, lung, and kidney, nourishes liver and kidney, replenishes blood and moistens intestines, and relaxes bowel, promotes lactation, and is used for essence and blood depletion and deficiency, dizziness, premature graying of hair, constipation, ischogalactia, infantile measles eruption, dry stool of the aged or the weak and other diseases.

Mulberry is sweet in flavor and cold in nature, acts on heart, liver, and kidney, nourishes yin and replenishes blood, moistens intestines, promotes the secretion of body fluid, and is used for yin-deletion blood depletion, yin-deficiency consumptive thirst, body fluid deletion thirst, vertigo and tinnitus, and constipation due to intestinal dryness.

Turtle shell gelatin is sweet and salty in flavor and slightly cold in nature, acts on liver, lung, and kidney, nourishes yin and allays fever, resolves hard lump, and is used for yin-deficiency hectic fever, consumptive disease and hemoptysis, chronic malaria, malaria with abdominal mass, hemorrhoids gall, and blood-deficiency amenorrhea.

Tortoise-plastron gelatin is sweet and salty in flavor and neutral in nature, nourishes yin, replenishes blood, stops bleeding, and is used for yin-deficiency blood depletion, consumptive heat and steaming bone, hematemesis, bleeding from five sense organs or subcutaneous tissue, dysphoria with smothery sensation and palpitation, kidney-deficiency backache, impotent feet and knees, metrorrhagia and metrostaxis, and leucorrhoea.

Donkey-hide gelatin is sweet in flavor and neutral in nature, acts on lung, liver, and kidney, replenishes blood and nourishes yin, moistens dryness, stops bleeding, and is used for blood-deficiency etiolation, vertigo and palpitation, dysphoria insomnia, and lung dryness cough.

American ginseng is sweet and slightly bitter in flavor and cool in nature, acts on heart, lung, and kidney, replenishes qi and nourishes yin, removes heat to promote the secretion of body fluid, and is used for yin-deficiency yin depletion, internal heat, asthma and bloody phlegm, deficiency-heat tiredness, consumptive thirst, and mouth dryness and throat dryness.

People with yin deficiency constitution often have the syndromes of yin-fluid deficiency and production of endogenous heat due to yin deficiency, which are usually represented by emaciation of the body, mouth dryness and throat dryness, tidal reddening of the cheeks, feverishness in palms and soles, tidal fever and night sweating, upset irritability, xerostomia, and dry and red tongue with little or even no coating. Yin deficiency in the five internal organs is clinically common, and besides the aforesaid clinical manifestations, corresponding lesions of each organ can be seen and therefore different symptoms appear. The conditioning of the yin deficiency constitution takes the principle of nourishing yin and conditioning the body. The present prescription mainly includes yin-nourishing drugs. As the yin deficiency constitution mainly results from long-term consumption of yin fluid in the body, most of the common yin-nourishing and tonifying materials are greasy and affect the transportation and transformation function of spleen and stomach. However, in the present prescription, drugs are selected based on the principle of being nourishing but not greasy, which are light and yin-nourishing materials in case that long-term administration of common yin-nourishing drugs increases greasiness and hurts stomach. And with the multiple types of drug materials of large dosages, efficacies of the various drug materials generate a synergistic effect, with the functions of nourishing yin of liver and kidney, and can be used for conditioning the yin deficiency constitution, so that people are vigorous with strong resistibility, and prevent diseases. With the conditioning for such constitution, it is more targeted and will not create side effects, without harm to the human body at all, and can achieve certain efficacy of strengthening the body.

As shown in FIG. 1, the processing method for the Chinese herbal oral paste for conditioning yin deficiency constitution of the present disclosure includes the following steps in sequence: preparation of materials, soaking, decoction, concentration, collecting an oral paste, and finally packaging. For specific operations of respective steps, reference can be made to various embodiments of the present disclosure.

Embodiment 1

A Chinese herbal oral paste for conditioning yin deficiency constitution includes the following components in parts by weight: 10 parts of coastal glehnia root, 2 parts of prepared rehmannia root, 5 parts of dogberry, 5 parts of Chinese yam, 6 parts of cortex moutan, 5 parts of fuling, 5 parts of radix asparagi, 1 part of fruit of Chinese magnoliavine, 5 parts of lycium barbarum, 4 parts of rhizoma alismatis, 10 parts of tremella, 3 parts of finger citron, 6 parts of fructus tribuli, 5 parts of ophiopogonis radix, 8 parts of glossy privet fruit, 1 part of amomum villosum, 10 parts of dendrobium nobile, 11 parts of lilium brownii, 5 parts of angelica, 7 parts of radix paeoniae alba, 1 part of licorice, 5 parts of radix scrophulariae, 2 parts of thunberg fritillary bulb, 5 parts of polygonatum odoratum, 7 parts of semen sesami nigrums, 5 parts of mulberry, 10 parts of turtle shell gelatin, 10 parts of tortoise-plastron gelatin, 4 parts of donkey-hide gelatin, 20 parts of xylitol, and 5 parts of American ginseng.

The processing method therefor includes the following steps in sequence:

preparation of materials: measuring raw materials of formula ratio according to composition of the Chinese herbal oral paste, and washing raw materials, except turtle shell gelatin, tortoise-plastron gelatin, donkey-hide gelatin, and xylitol, for subsequent use;

soaking: soaking the cleaned raw materials with 8 folds of water for 8 h, with the water over the raw materials by 10 cm;

decoction: decocting the soaked drug materials over flame, firstly boiling the drug materials with high heat to sufficiently expand, then boiling the drug materials with low heat for 1 hour of decoction, then filtering drug juice with gauze, then soaking filtered dregs of decoction with clear water and decocting the soaked dregs of decoction with low heat for 1 hour, thus repeating 4 times, then combining the filtered drug juice, and squeezing and filtering the dregs to obtain squeezed juice; combining the decoction juice with the squeezed juice, followed by static settlement for 2 h, and filtering, to obtain a supernatant liquid for subsequent use;

concentration: boiling and skimming the supernatant liquid resulted in the decoction step, followed by stirring while decocting and concentrating with low heat, until a drug liquid does not disperse when being dropped on paper, to obtain a vegetarian paste;

collecting an oral paste: pouring xylitol, melted turtle shell gelatin, tortoise-plastron gelatin, and donkey-hide gelatin into the vegetarian paste respectively, stirring them continuously with a shovel while cooking them slowly with low heat, until the juice can coagulate into bead and not disperse s when being dropped into clear water, then canning the resulted oral paste.

In the above, the step of melting gelatin type drugs is: smashing lumps of turtle shell gelatin, tortoise-plastron gelatin, and donkey-hide gelatin into small gelatin pieces or gelatin powder, soaking and softening the small gelatin pieces or the gelatin powder in Shaoxing wine, water bath heating the softened small gelatin pieces or gelatin powder in a steamer until they are completely melted.

Embodiment 2

A Chinese herbal oral paste for conditioning yin deficiency constitution includes the following components in parts by weight: 30 parts of coastal glehnia root, 25 parts of prepared rehmannia root, 25 parts of dogberry, 25 parts of Chinese yam, 16 parts of cortex moutan, 15 parts of fuling, 15 parts of radix asparagi, 5 parts of fruit of Chinese magnoliavine, 15 parts of lycium barbarum, 12 parts of rhizoma alismatis, 30 parts of tremella, 9 parts of finger citron, 24 parts of fructus tribuli, 15 parts of ophiopogonis radix, 22 parts of glossy privet fruit, 5 parts of amomum villosum, 30 parts of dendrobium nobile, 29 parts of lilium brownii, 15 parts of angelica, 23 parts of radix paeoniae alba, 5 parts of licorice, 15 parts of radix scrophulariae, 10 parts of thunberg fritillary bulb, 15 parts of polygonatum odoratum, 23 parts of semen sesami nigrums, 15 parts of mulberry, 30 parts of turtle shell gelatin, 30 parts of tortoise-plastron gelatin, 17 parts of donkey-hide gelatin, 40 parts of xylitol, and 15 parts of American ginseng.

The processing method therefor includes the following steps in sequence:

preparation of materials: measuring raw materials of formula ratio according to composition of the Chinese herbal oral paste, and washing raw materials, except turtle shell gelatin, tortoise-plastron gelatin, donkey-hide gelatin, and xylitol, for subsequent use;

soaking: soaking the cleaned raw materials with 10 folds of water for 15 h, with the water over the raw materials by 20 cm;

decoction: decocting the soaked drug materials over flame, firstly boiling the drug materials with high heat to sufficiently expand, then boiling the drug materials with low heat for 2 hours of decoction, then filtering drug juice with gauze, then soaking filtered dregs of decoction with clear water and decocting the soaked dregs of decoction with low heat for 1 hour, thus repeating 2 times, then combining the filtered drug juice, and squeezing and filtering the dregs to obtain squeezed juice; combining the decoction juice with the squeezed juice, followed by static settlement for 2 h, and filtering, to obtain a supernatant liquid for subsequent use;

concentration: boiling and skimming the supernatant liquid resulted in the decoction step, followed by stirring while decocting and concentrating with low heat, until a drug liquid does not disperse when being dropped on paper, to obtain a vegetarian paste;

collecting an oral paste: pouring xylitol, melted turtle shell gelatin, tortoise-plastron gelatin, and donkey-hide gelatin into the vegetarian paste respectively, stirring them continuously with a shovel while cooking them slowly with low heat, until the juice can coagulate into beads and not disperse when being dropped into clear water, then canning the resulted oral paste.

In the above, the step of melting gelatin type drugs is: smashing lumps of turtle shell gelatin, tortoise-plastron gelatin, and donkey-hide gelatin into small gelatin pieces or gelatin powder, soaking and softening the small gelatin pieces or the gelatin powder in Shaoxing wine, water bath heating the softened small gelatin pieces or gelatin powder in a steamer until they are completely melted.

Embodiment 3

A Chinese herbal oral paste for conditioning yin deficiency constitution includes the following components in parts by weight: 15 parts of coastal glehnia root, 10 parts of prepared rehmannia root, 10 parts of dogberry, 10 parts of Chinese yam, 7 parts of cortex moutan, 7 parts of fuling, 7 parts of radix asparagi, 2 parts of fruit of Chinese magnoliavine, 7 parts of lycium barbarum, 6 parts of rhizoma alismatis, 15 parts of tremella, 4 parts of finger citron, 10 parts of fructus tribuli, 7 parts of ophiopogonis radix, 11 parts of glossy privet fruit, 2 parts of amomum villosum, 15 parts of dendrobium nobile, 15 parts of lilium brownii, 7 parts of angelica, 10 parts of radix paeoniae alba, 2 parts of licorice, 7 parts of radix scrophulariae, 4 parts of thunberg fritillary bulb, 7 parts of polygonatum odoratum, 10 parts of semen sesami nigrums, 7 parts of mulberry, 15 parts of turtle shell gelatin, 15 parts of tortoise-plastron gelatin, 7 parts of donkey-hide gelatin, 25 parts of xylitol, and 7 parts of American ginseng.

The processing method therefor includes the following steps in sequence:

preparation of materials: measuring raw materials of formula ratio according to composition of the Chinese herbal oral paste, and washing raw materials, except turtle shell gelatin, tortoise-plastron gelatin, donkey-hide gelatin, and xylitol, for subsequent use;

soaking: soaking the cleaned raw materials with 9 folds of water for 9 h, with the water over the raw materials by 13 cm;

decoction: decocting the soaked drug materials over flame, firstly boiling the drug materials with high heat to sufficiently expand, then boiling the drug materials with low heat for 1.5 hours of decoction, then filtering drug juice with gauze, then soaking filtered dregs of decoction with clear water and decocting the soaked dregs of decoction with low heat for 1 hour, thus repeating 3 times, then combining the filtered drug juice, and squeezing and filtering the dregs to obtain squeezed juice; combining the decoction juice with the squeezed juice, followed by static settlement for 2 h, and filtering, to obtain a supernatant liquid for subsequent use;

concentration: boiling and skimming the supernatant liquid resulted in the decoction step, followed by stirring while decocting and concentrating with low heat, until a drug liquid does not disperse when being dropped on paper, to obtain a vegetarian paste;

collecting an oral paste: pouring xylitol, and melted turtle shell gelatin, tortoise-plastron gelatin, and donkey-hide gelatin into the vegetarian paste respectively, stirring them continuously with a shovel while cooking them slowly with low heat, until the juice can coagulate into beads and not disperse when being dropped into clear water, then canning the resulted oral paste.

In the above, the step of melting gelatin type drugs is: smashing lumps of turtle shell gelatin, tortoise-plastron gelatin, and donkey-hide gelatin into small gelatin pieces or gelatin powder, soaking and softening the small gelatin pieces or the gelatin powder in Shaoxing wine, water bath heating the softened small gelatin pieces or gelatin powder in a steamer until they are completely melted.

Embodiment 4

A Chinese herbal oral paste for conditioning yin deficiency constitution includes the following components in parts by weight: 25 parts of coastal glehnia root, 20 parts of prepared rehmannia root, 20 parts of dogberry, 20 parts of Chinese yam, 13 parts of cortex moutan, 13 parts of fuling, 13 parts of radix asparagi, 4 parts of fruit of Chinese magnoliavine, 13 parts of lycium barbarum, 10 parts of rhizoma alismatis, 25 parts of tremella, 8 parts of finger citron, 20 parts of fructus tribuli, 13 parts of ophiopogonis radix, 19 parts of glossy privet fruit, 4 parts of amomum villosum, 25 parts of dendrobium nobile, 25 parts of lilium brownii, 13 parts of angelica, 20 parts of radix paeoniae alba, 4 parts of licorice, 13 parts of radix scrophulariae, 8 parts of thunberg fritillary bulb, 13 parts of polygonatum odoratum, 20 parts of semen sesami nigrums, 13 parts of mulberry, 25 parts of turtle shell gelatin, 25 parts of tortoise-plastron gelatin, 13 parts of donkey-hide gelatin, 35 parts of xylitol, and 13 parts of American ginseng.

The processing method therefor includes the following steps in sequence:

preparation of materials: measuring raw materials of formula ratio according to composition of the Chinese herbal oral paste, and washing raw materials, except turtle shell gelatin, tortoise-plastron gelatin, donkey-hide gelatin, and xylitol, for subsequent use;

soaking: soaking the cleaned raw materials with 9 folds of water for 13 h, with the water over the raw materials by 15 cm;

decoction: decocting the soaked drug materials over flame, firstly boiling the drug materials with high heat to sufficiently expand, then boiling the drug materials with low heat for 1.5 hours of decoction, then filtering drug juice with gauze, then soaking filtered dregs of decoction with clear water and decocting the soaked dregs of decoction with low heat for 1 hour, thus repeating 3 times, then combining the filtered drug juice, and squeezing and filtering the dregs to obtain squeezed juice; combining the decoction juice with the squeezed juice, followed by static settlement for 2 h, and filtering, to obtain a supernatant liquid for subsequent use;

concentration: boiling and skimming the supernatant liquid resulted in the decoction step, followed by stirring while decocting and concentrating with low heat, until a drug liquid does not disperse when being dropped on paper, to obtain a vegetarian paste;

collecting an oral paste: pouring xylitol, melted turtle shell gelatin, tortoise-plastron gelatin, and donkey-hide gelatin into the vegetarian paste respectively, stirring them continuously with a shovel while cooking them slowly with low heat, until the juice can coagulate into beads and not disperse when being dropped into clear water, then canning the resulted oral paste.

In the above, the step of melting gelatin type drugs is: smashing lumps of turtle shell gelatin, tortoise-plastron gelatin, and donkey-hide gelatin into small gelatin pieces or gelatin powder, soaking and softening the small gelatin pieces or the gelatin powder in Shaoxing wine, water bath heating the softened small gelatin pieces or gelatin powder in a steamer until they are completely melted.

Embodiment 5

A Chinese herbal oral paste for conditioning yin deficiency constitution includes the following components in parts by weight: 20 parts of coastal glehnia root, 15 parts of prepared rehmannia root, 15 parts of dogberry, 15 parts of Chinese yam, 10 parts of cortex moutan, 10 parts of fuling, 10 parts of radix asparagi, 3 parts of fruit of Chinese magnoliavine, 10 parts of lycium barbarum, 8 parts of rhizoma alismatis, 20 parts of tremella, 6 parts of finger citron, 16 parts of fructus tribuli, 10 parts of ophiopogonis radix, 15 parts of glossy privet fruit, 3 parts of amomum villosum, 20 parts of dendrobium nobile, 20 parts of lilium brownii, 10 parts of angelica, 15 parts of radix paeoniae alba, 3 parts of licorice, 10 parts of radix scrophulariae, 6 parts of thunberg fritillary bulb, 10 parts of polygonatum odoratum, 15 parts of semen sesami nigrums, 10 parts of mulberry, 20 parts of turtle shell gelatin, 20 parts of tortoise-plastron gelatin, 10 parts of donkey-hide gelatin, 30 parts of xylitol, and 10 parts of American ginseng.

The processing method therefor includes the following steps in sequence:

preparation of materials: measuring raw materials of formula ratio according to composition of the Chinese herbal oral paste, and washing raw materials, except turtle shell gelatin, tortoise-plastron gelatin, donkey-hide gelatin, and xylitol, for subsequent use;

soaking: soaking the cleaned raw materials with 9 folds of water for 13 h, with the water over the raw materials by 15 cm;

decoction: decocting the soaked drug materials over flame, firstly boiling the drug materials with high heat to sufficiently expand, then boiling the drug materials with low heat for 1.5 hours of decoction, then filtering drug juice with gauze, then soaking filtered dregs of decoction with clear water and decocting the soaked dregs of decoction with low heat for 1 hour, thus repeating 3 times, then combining the filtered drug juice, and squeezing and filtering the dregs to obtain squeezed juice; combining the decoction juice with the squeezed juice, followed by static settlement for 2 h, and filtering, to obtain a supernatant liquid for subsequent use;

concentration: boiling and skimming the supernatant liquid resulted in the decoction step, followed by stirring while decocting and concentrating with low heat, until a drug liquid does not disperse when being dropped on paper, to obtain a vegetarian paste;

collecting an oral paste: pouring xylitol, melted turtle shell gelatin, tortoise-plastron gelatin, and donkey-hide gelatin into the vegetarian paste respectively, stirring them continuously with a shovel while cooking them slowly with low heat, until the juice can coagulate into beads and not disperse when being dropped into clear water, then canning the resulted oral paste.

In the above, the step of melting gelatin type drugs is: smashing lumps of turtle shell gelatin, tortoise-plastron gelatin, and donkey-hide gelatin into small gelatin pieces or gelatin powder, soaking and softening the small gelatin pieces or the gelatin powder in Shaoxing wine, water bath heating the softened small gelatin pieces or gelatin powder in a steamer until they are completely melted.

Experiment Example 1: the followings are a test of effects of the Chinese herbal oral paste for conditioning yin deficiency constitution prepared according to Embodiment 5 of the present disclosure.

Basic conditions of cases: 150 clinical cases of yin deficiency constitution, including 80 male cases and 70 female cases. 20 cases suffered from dry cough, had reduced sticky and white sputum, or had blood-tinged sputum, laryngoxerosis, red tongue with scant liquid, and thready and rapid pulse; 20 cases suffered from insomnia and dreamful sleep, dysphoria in five centers, palpitation, red tongue with scant liquid, and thready and rapid pulse; 20 cases suffered from anorexia, hard bound stool, mouth and lip dryness, or even retching, red tongue with scant liquid, and thread and rapid pulse; 20 cases suffered from dryness in the eyes, headache and vertigo, blurred vision, red tongue with scant liquid, and thready and rapid pulse; 20 cases suffered from lumbago and weakness of the legs, dizziness and tinnitus, spermatorrhea and amnesia, oliguria, hair and skin dryness, red tongue with scant liquid, with little or even no coating, and thready and rapid pulse; 50 cases had other symptoms of yin deficiency constitution.

Usage and dosage: 25 g each time, once a day. Brew 25 g of the oral paste with boiling water in a cup, and stirring them to make the oral paste melt for administration.

Evaluation criteria for therapeutic effects:

Cured: clinical symptoms were completely eliminated, and normal life was restored.

Effective: clinical symptoms were partially eliminated, and various signs were gradually improved.

Ineffective: symptoms and signs were not obviously improved.

Result statistics: 91 cases cured, effective to 39 cases, and ineffective to 20 cases, i.e., effective to 130 cases in total, therefore the total effective rate was 86.67%.

Experiment Example 2: experimental study on a product of the present disclosure in assisting mice in improving yin deficiency syndrome (1) Experimental principle:

Pathological models of mice suffering from yin deficiency were prepared with thyroxine in combination with reserpine, and the effects of the drugs for improving the yin-deficiency mice were evaluated through an anti-fatigue test.

(2) Experimental materials:

The Chinese herbal oral pastes prepared according to Embodiments 1-5.

Experimental animals: ICR mice, 200±20 g.

(3) Test method:

70 ICR mice were divided into seven groups randomly, which were a normal control group, a yin-deficiency model group, and experimental groups of Embodiments 1-5 (dosage: 0.4 g/kg), and the Chinese herbal oral paste was intragastrically administered to each group for four weeks. After 20 days of intragastric administration, all the groups, except the normal control group, were intragastrically administered with thyroxine (3 mg per mouse) plus reserpine (0.02 mg per mouse), once a day for 10 times continuously. Half an hour after the last administration, the tail of each of the mice was loaded with solder wires having a weight of 10% of the body weight of the mouse, then the mice were put into room temperature (25° C.) water, and the survival times of the mice were measured.

(4) Statistical method

Calculated data were expressed by average±standard deviations, t test was used for intergroup difference comparison, and results were obtained by using EXCEL statistical software. $p<0.05$ means that there is a significant difference, and $p<0.01$ means that there is an extremely significant difference.

(5) The experimental results are shown in table 1.

TABLE 1

Impact of the Product on Loaded Swimming Time of Mice

| Group | Loaded Swimming Time (s) |
| --- | --- |
| Normal Control Group | 153 ± 11.9 |
| Yin-deficiency Model Group | 85 ± 12.3 |
| Embodiment 1 | 151 ± 15.4* |
| Embodiment 2 | 150 ± 13.8* |
| Embodiment 3 | 143 ± 14.7* |
| Embodiment 4 | 147 ± 12.1* |
| Embodiment 5 | 152 ± 14.4* |

Compared with the model group, *$p<0.05$, which means that there is a significance difference.

The experimental data show that: the Chinese herbal oral pastes corresponding to Embodiments 1-5 can increase the loaded swimming time of the mice, and have the effect of improving the physical fatigue of the yin-deficiency model mice.

It should be indicated that Embodiments 1-5 of the present invention are merely some of the embodiments for implementing the technical solutions of the present invention, and should not be construed as the scope of protection of the present invention merely limited to the above five embodiments, and a person skilled in the art can make further improvements on the basis of the present invention without departing from the principle and spirit of the present invention.

For example, the components of the Chinese herbal oral paste of the present invention are not limited to those listed in respective embodiments, while other Chinese herbal medicines also can be added, to further perfecting the drug formulation of the Chinese herbal oral paste of the present invention.

For another example, in the process of the processing method for the Chinese herbal oral paste of the present invention, in the concentration step, when the drug juice is concentrated to the vegetarian paste, a wild jujube shell powder is added evenly with stirring. The wild jujube shell powder above is obtained by sufficiently smashing and grinding the wild jujube shell, with a particle size of 100-400 micrometers. The wild jujube shell powder has the main components of cellulose and lignin, has quite advanced pores in the powder particles, and is a natural drug carrier.

When added to the Chinese herbal oral paste, the pores inside the wild jujube shell powder will be filled up with the drug components of the Chinese herbal oral paste. Since the cellulose and lignin cannot be digested or absorbed in vivo, they can be effective as sustained release, then a small part of the drug components stored in the wild jujube shell powder can be released continuously, so that the drug is present in the digestive system for an extended period of time. The phenomenon that the drug components are wasted as the digestive system cannot absorb a large amount of drug components within a short period of time will not occur. The wild jujube shell powder is added in an amount of 1%-3% of the gelatin type drugs, and should not be used in an excessive amount, because the excessive amount, on one hand, will deteriorate the form quality of the oral paste, and on the other hand, will increase the burdens of the intestines and stomach as it cannot be absorbed by the human body.

The descriptions above are only preferred embodiments of the present invention, which are not used to limit the present invention. For a person skilled in the art, the present invention may have various changes and variations. Any modifications, equivalent substitutions, improvements etc. within the spirit and principle of the present invention shall all be included in the scope of protection of the present invention.

What is claimed is:

1. A Chinese herbal oral paste for conditioning yin deficiency constitution, comprising the following components in parts by weight: 10-30 parts of coastal glehnia root, 2-25 parts of prepared rehmannia root, 5-25 parts of dogberry, 5-25 parts of Chinese yam, 6-16 parts of cortex moutan, 5-15 parts of fuling, 5-15 parts of radix asparagi, 1-5 parts of fruit of Chinese magnoliavine, 5-15 parts of lycium barbarum, 4-12 parts of rhizoma alismatis, 10-30 parts of tremella, 3-9 parts of finger citron, 6-24 parts of fructus tribuli, 5-15 parts of ophiopogonis radix, 8-22 parts of glossy privet fruit, 1-5 parts of amomum villosum, 10-30 parts of dendrobium nobile, 11-29 parts of lilium brownii, 5-15 parts of angelica, 7-23 parts of radix paeoniae alba, 1-5 parts of licorice, 5-15 parts of radix scrophulariae, 2-10 parts of thunberg fritillary bulb, 5-15 parts of polygonatum odoratum, 7-23 parts of semen sesami nigrums, 5-15 parts of mulberry, 10-30 parts of turtle shell gelatin, 10-30 parts of tortoise-plastron gelatin, 4-17 parts of donkey-hide gelatin, 20-40 parts of xylitol, and 5-15 parts of American ginseng.

2. The Chinese herbal oral paste for conditioning yin deficiency constitution of claim 1, wherein the coastal glehnia root is 15-25 parts by weight, the prepared rehmannia root is 10-20 parts by weight, the dogberry is 10-20 parts by weight, the Chinese yam is 10-20 parts by weight, the cortex moutan is 7-13 parts by weight, the fuling is 7-13 parts by weight, the radix asparagi is 7-13 parts by weight, the fruit of Chinese magnoliavine is 2-4 parts by weight, the lycium barbarum is 7-13 parts by weight, the rhizoma alismatis is 6-10 parts by weight, the tremella is 15-25 parts by weight, the finger citron is 4-8 parts by weight, the fructus tribuli is 10-20 parts by weight, the ophiopogonis radix is 7-13 parts by weight, the glossy privet fruit is 11-19 parts by weight, the amomum villosum is 2-4 parts by weight, the dendrobium nobile is 15-25 parts by weight, the lilium brownii is 15-25 parts by weight, the angelica is 7-13 parts by weight, the radix paeoniae alba is 10-20 parts by weight, the licorice is 2-4 parts by weight, the radix scrophulariae is 7-13 parts by weight, the thunberg fritillary bulb is 4-8 parts by weight, the polygonatum odoratum is 7-13 parts by weight, the semen sesami nigrums is 10-20 parts by weight, the mulberry is 7-13 parts by weight, the turtle shell gelatin is 15-25 parts by weight, the tortoise-plastron gelatin is 15-25 parts by weight, the donkey-hide gelatin is 7-13 parts by weight, the xylitol is 25-35 parts by weight, and the American ginseng is 7-13 parts by weight.

3. The Chinese herbal oral paste for conditioning yin deficiency constitution of claim 1, wherein the coastal glehnia root is 20 parts by weight, the prepared rehmannia root is 15 parts by weight, the parts of dogberry is 15 parts by weight, the Chinese yam is 15 parts by weight, the cortex moutan is 10 parts by weight, the fuling is 10 parts by weight, the radix asparagi is 10 parts by weight, the fruit of Chinese magnoliavine is 3 parts by weight, the lycium barbarum is 10 parts by weight, the rhizoma alismatis is 8 parts by weight, the tremella is 20 parts by weight, the finger citron is 6 parts by weight, the fructus tribuli is 15 parts by weight, the ophiopogonis radix is 10 parts by weight, the glossy privet fruit is 15 parts by weight, the amomum villosum is 3 parts by weight, the dendrobium nobile is 20 parts by weight, the lilium brownii is 20 parts by weight, the angelica is 10 parts by weight, the radix paeoniae alba is 15 parts by weight, the licorice is 3 parts by weight, the radix scrophulariae is 10 parts by weight, the thunberg fritillary bulb is 6 parts by weight, the polygonatum odoratum is 10 parts by weight, the semen sesami nigrums is 15 parts by weight, the mulberry is 10 parts by weight, the turtle shell gelatin is 20 parts by weight, the tortoise-plastron gelatin is 20 parts by weight, the donkey-hide gelatin is 10 parts by weight, the xylitol is 30 parts by weight, and the American ginseng is 10 parts by weight.

4. A processing method for the Chinese herbal oral paste for conditioning yin deficiency constitution of claim 1, comprising the following steps in sequence: preparation of materials, soaking, decoction, concentration, and collecting an oral paste.

5. The processing method for the Chinese herbal oral paste for conditioning yin deficiency constitution of claim 4, wherein the step of preparation of materials is: measuring raw materials of formula ratio according to composition of the Chinese herbal oral paste, and washing raw materials, except turtle shell gelatin, tortoise-plastron gelatin, donkey-hide gelatin, and xylitol, for subsequent use.

6. The processing method for the Chinese herbal oral paste for conditioning yin deficiency constitution of claim 5, wherein the soaking step is: soaking the cleaned raw materials with 8-10 folds of water for 8-15 h, with the water over the raw materials by 10-20 cm.

7. The processing method for the Chinese herbal oral paste for conditioning yin deficiency constitution of claim 6, wherein the decoction step is: decocting the soaked drug materials over flame, firstly boiling the drug materials with high heat to sufficiently expand, then boiling the drug materials with low heat for 1-2 hours of decoction, then filtering drug juice with gauze, then soaking filtered dregs of decoction with clear water and decocting the soaked dregs of decoction with low heat for 1 hour, thus repeating 2-4 times, then combining the filtered drug juice, and squeezing and filtering the dregs to obtain a squeezed juice; combining the decoction juice with the squeezed juice, followed by static settlement for 2 h, and filtering, to obtain a supernatant liquid for subsequent use.

8. The processing method for the Chinese herbal oral paste for conditioning yin deficiency constitution of claim 7, wherein the concentration step is: boiling and skimming the supernatant liquid resulted in the decoction step, followed by stirring while decocting and concentrating with low heat, until a drug liquid does not disperse when being dropped on paper, to obtain a vegetarian paste.

9. The processing method for the Chinese herbal oral paste for conditioning yin deficiency constitution of claim 8, wherein the step of collecting an oral paste is: pouring xylitol, melted turtle shell gelatin, tortoise-plastron gelatin, and donkey-hide gelatin into the vegetarian paste respectively, stirring them continuously with a shovel while cooking them slowly with low heat, until the juice can coagulate into beads and not disperse when being dropped into clear water, then canning the resulted oral paste.

10. The processing method for the Chinese herbal oral paste for conditioning yin deficiency constitution of claim 9, wherein the melting step is: smashing lumps of turtle shell gelatin, tortoise-plastron gelatin, and donkey-hide gelatin into small gelatin pieces or gelatin powder, soaking and softening the small gelatin pieces or the gelatin powder in Shaoxing wine, water bath heating the softened small gelatin pieces or gelatin powder in a steamer until they are completely melted.

11. A processing method for the Chinese herbal oral paste for conditioning yin deficiency constitution of claim 2, comprising the following steps in sequence: preparation of materials, soaking, decoction, concentration, and collecting an oral paste.

12. The processing method for the Chinese herbal oral paste for conditioning yin deficiency constitution of claim 11, wherein the step of preparation of materials is: measuring raw materials of formula ratio according to composition of the Chinese herbal oral paste, and washing raw materials, except turtle shell gelatin, tortoise-plastron gelatin, donkey-hide gelatin, and xylitol, for subsequent use.

13. The processing method for the Chinese herbal oral paste for conditioning yin deficiency constitution of claim 12, wherein the soaking step is: soaking the cleaned raw materials with 8-10 folds of water for 8-15 h, with the water over the raw materials by 10-20 cm.

14. The processing method for the Chinese herbal oral paste for conditioning yin deficiency constitution of claim 13, wherein the decoction step is: decocting the soaked drug materials over flame, firstly boiling the drug materials with high heat to sufficiently expand, then boiling the drug materials with low heat for 1-2 hours of decoction, then filtering drug juice with gauze, then soaking filtered dregs of decoction with clear water and decocting the soaked dregs of decoction with low heat for 1 hour, thus repeating 2-4 times, then combining the filtered drug juice, and squeezing and filtering the dregs to obtain a squeezed juice; combining the decoction juice with the squeezed juice, followed by static settlement for 2 h, and filtering, to obtain a supernatant liquid for subsequent use.

15. The processing method for the Chinese herbal oral paste for conditioning yin deficiency constitution of claim 14, wherein the concentration step is: boiling and skimming the supernatant liquid resulted in the decoction step, followed by stirring while decocting and concentrating with low heat, until a drug liquid does not disperse when being dropped on paper, to obtain a vegetarian paste.

16. The processing method for the Chinese herbal oral paste for conditioning yin deficiency constitution of claim 15, wherein the step of collecting an oral paste is: pouring xylitol, melted turtle shell gelatin, tortoise-plastron gelatin, and donkey-hide gelatin into the vegetarian paste respectively, stirring them continuously with a shovel while cooking them slowly with low heat, until the juice can coagulate into beads and not disperse when being dropped into clear water, then canning the resulted oral paste.

17. The processing method for the Chinese herbal oral paste for conditioning yin deficiency constitution of claim 16, wherein the melting step is: smashing lumps of turtle shell gelatin, tortoise-plastron gelatin, and donkey-hide gelatin into small gelatin pieces or gelatin powder, soaking and softening the small gelatin pieces or the gelatin powder in Shaoxing wine, water bath heating the softened small gelatin pieces or gelatin powder in a steamer until they are completely melted.

18. A processing method for the Chinese herbal oral paste for conditioning yin deficiency constitution of claim 3, comprising the following steps in sequence: preparation of materials, soaking, decoction, concentration, and collecting an oral paste.

19. The processing method for the Chinese herbal oral paste for conditioning yin deficiency constitution of claim 18, wherein the step of preparation of materials is: measuring raw materials of formula ratio according to composition of the Chinese herbal oral paste, and washing raw materials, except turtle shell gelatin, tortoise-plastron gelatin, donkey-hide gelatin, and xylitol, for subsequent use.

20. The processing method for the Chinese herbal oral paste for conditioning yin deficiency constitution of claim 19, wherein the soaking step is: soaking the cleaned raw materials with 8-10 folds of water for 8-15 h, with the water over the raw materials by 10-20 cm.

* * * * *